US012758107B2

(12) United States Patent
Tada

(10) Patent No.: US 12,758,107 B2
(45) Date of Patent: Oct. 13, 2026

(54) DETECTION DEVICE

(71) Applicant: Japan Display Inc., Tokyo (JP)

(72) Inventor: Masahiro Tada, Tokyo (JP)

(73) Assignee: Japan Display Inc., Tokyo (JP)

( * ) Notice: Subject to any disclaimer, the term of this patent is extended or adjusted under 35 U.S.C. 154(b) by 438 days.

(21) Appl. No.: 18/221,608

(22) Filed: Jul. 13, 2023

(65) Prior Publication Data

US 2024/0023818 A1 Jan. 25, 2024

(30) Foreign Application Priority Data

Jul. 19, 2022 (JP) ................................ 2022-115041

(51) Int. Cl.
*A61B 5/021* (2006.01)
*A61B 5/024* (2006.01)

(52) U.S. Cl.
CPC ...... *A61B 5/02108* (2013.01); *A61B 5/02438* (2013.01)

(58) Field of Classification Search
None
See application file for complete search history.

(56) References Cited

U.S. PATENT DOCUMENTS

2015/0220109 A1* 8/2015 von Badinski .... G02B 19/0052 368/10
2017/0049340 A1* 2/2017 Cho ..................... A61B 5/0285
2018/0103868 A1* 4/2018 Seko ...................... A61B 5/681
2018/0241250 A1* 8/2018 Kahlman ................. H04B 5/26
2022/0320899 A1* 10/2022 Sanchez ................ H02J 50/001
2023/0095971 A1* 3/2023 He ......................... A61B 5/282 600/301

FOREIGN PATENT DOCUMENTS

JP 2017-506376 A 3/2017
WO 2015/081321 A1 6/2015

OTHER PUBLICATIONS

Office Action issued in related Japanese Patent Application No. 2022-115041 issued on Oct. 28, 2025 and English translation of same. 6 pages.
Office Action issued in related Japanese Patent Application No. 2022-115041 issued on Mar. 3, 2026 and English translation of same. 5 pages.

* cited by examiner

*Primary Examiner* — Michael R Bloch
(74) *Attorney, Agent, or Firm* — K&L Gates LLP

(57) ABSTRACT

According to an aspect, a detection device that is wearable on one finger includes: a first electrode having an inner surface to be in contact with a finger wearing the detection device; a second electrode provided outside the first electrode and electrically insulated from the first electrode; a light source provided outside the first electrode and inside the second electrode and configured to irradiate the finger with light; a light sensor provided outside the first electrode and inside the second electrode and configured to receive light from the finger; and a control circuit provided outside the first electrode and inside the second electrode and configured to measure biological information based on an output from the light sensor. The light source includes at least one of a red light source, an infrared light source, a near-infrared light source, and a green light source.

15 Claims, 15 Drawing Sheets

DETECTION DEVICE

CROSS-REFERENCE TO RELATED APPLICATION

This application claims the benefit of priority from Japanese Patent Application No. 2022-115041 filed on Jul. 19, 2022, the entire contents of which are incorporated herein by reference.

BACKGROUND

1. Technical Field

What is disclosed herein relates to a detection device.

2. Description of the Related Art

Arteriosclerosis is known to be one of factors of cerebral and myocardial infarctions. Thus, the occurrence of cerebral and myocardial infarctions can be prevented by anticipating and addressing arteriosclerosis in advance. Arteriosclerosis can be estimated by measuring pulse wave propagation velocity. There is a known oxygen saturation measurement device that is worn on a finger of a living body and measures the oxygen saturation based on a pulse wave measured from an artery of the finger of the living body (for example, Japanese Patent No. 4739126).

An electrocardiograph or a fingertip-mounted photoelectric sensor is needed to measure the pulse wave propagation velocity. In such cases, the device for the measurement is large and it is difficult to easily measure the pulse wave propagation velocity at all times.

For the foregoing reasons, there is a need for a detection device with which vital data such as pulse wave velocity and blood pressure can be easily measured at all times.

SUMMARY

According to an aspect, a detection device that is wearable on one finger includes: a first electrode having an inner surface to be in contact with a finger wearing the detection device; a second electrode provided outside the first electrode and electrically insulated from the first electrode; a light source provided outside the first electrode and inside the second electrode and configured to irradiate the finger with light; a light sensor provided outside the first electrode and inside the second electrode and configured to receive light from the finger; and a control circuit provided outside the first electrode and inside the second electrode and configured to measure biological information based on an output from the light sensor. The light source includes at least one of a red light source, an infrared light source, a near-infrared light source, and a green light source.

DETAILED DESCRIPTION

Aspects (embodiments) of the present disclosure will be described below in detail with reference to the accompanying drawings. Contents described below in the embodiments do not limit the present disclosure. Components described below include those that could be easily thought of by the skilled person in the art and those identical in effect. Components described below may be combined as appropriate. What is disclosed herein is merely exemplary, and any modification that could be easily thought of by the skilled person in the art as appropriate without departing from the gist of the disclosure is contained in the scope of the present disclosure. For clearer description, the drawings are schematically illustrated for the width, thickness, shape, and the like of each component as compared to an actual aspect in some cases, but the drawings are merely exemplary and do not limit interpretation of the present disclosure. In the present specification and drawings, any element the same as that already described with reference to an already described drawing is denoted by the same reference sign, and detailed description thereof is omitted as appropriate in some cases.

Configuration of Detection Device

Figure 1:
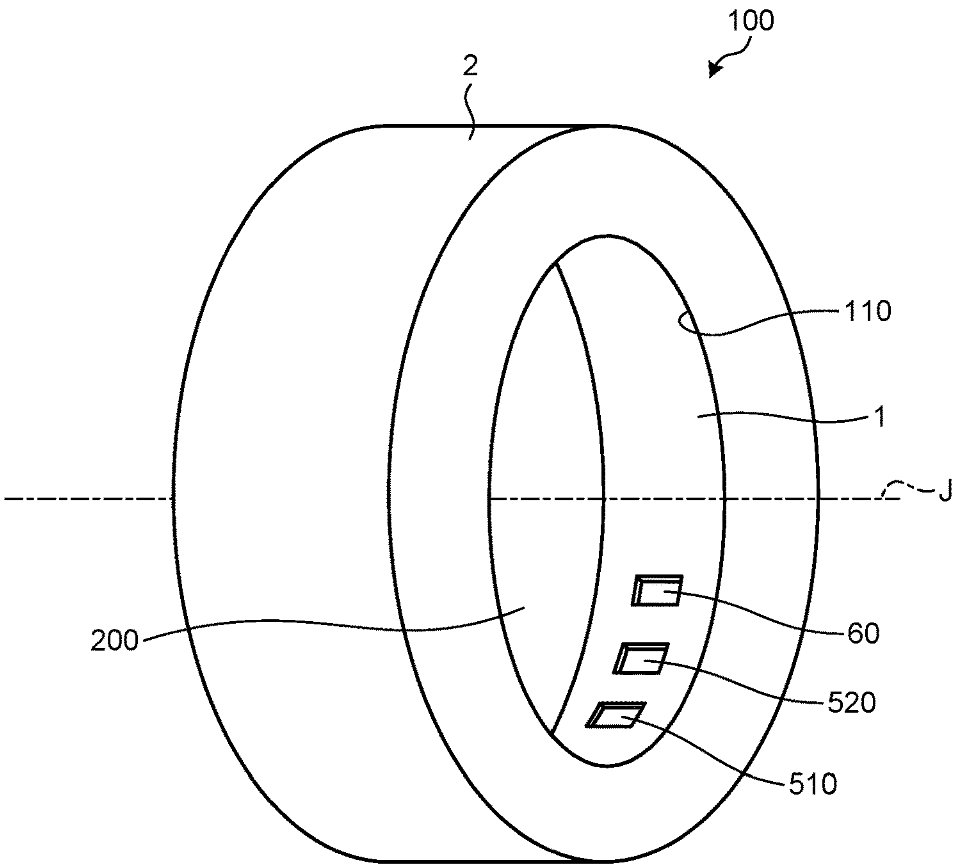
FIG. 1 is an external view of a detection device according to an embodiment.

FIG. 1 is an external view of a detection device according to an embodiment. In FIG. 1, a detection device 100 has a finger-ring shape. The detection device 100 includes a hollow 200. A finger can be inserted into the hollow 200 of the detection device 100. Thus, a user of the detection device 100 can wear the detection device 100 on one finger.

In FIG. 1, the detection device 100 includes an inner electrode 1 as a first electrode and an outer electrode 2 as a second electrode. The inner electrode 1 is an electric conductor that contacts a finger when the detection device 100 is worn on the finger. The inner electrode 1 contacts a finger when the detection device 100 is worn on the finger. Specifically, the inner electrode 1 has an inner surface 110 for contacting a finger wearing the detection device 100. The inner electrode 1 includes a plurality of openings 60, 510, 520, and the like as described later.

The outer electrode 2 is provided outside the inner electrode 1. The outer electrode 2 is electrically insulated from the inner electrode 1.

Figure 2:
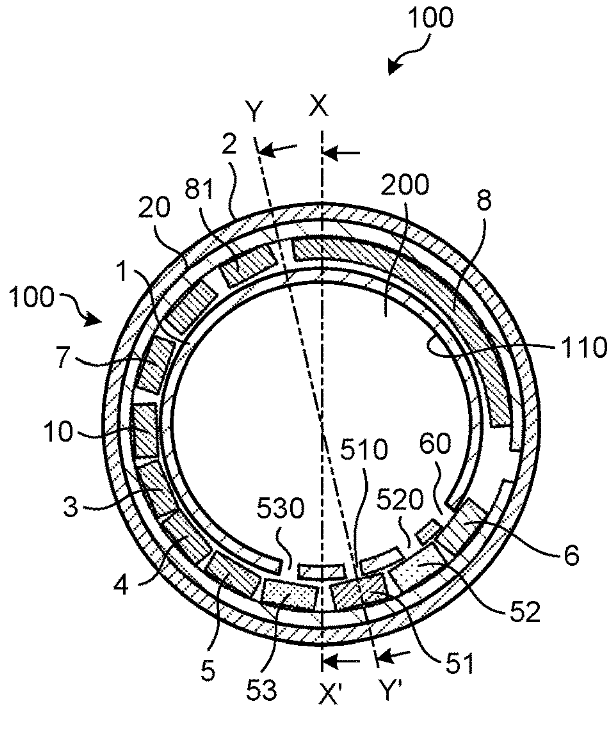
FIG. 2 is an internal view of a structure of the detection device in FIG. 1.
Figure 3:
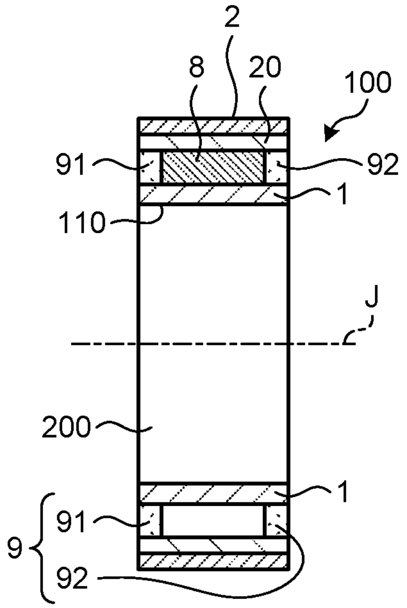
FIG. 3 is a sectional view taken along line X-X' in FIG. 2.
Figure 4:
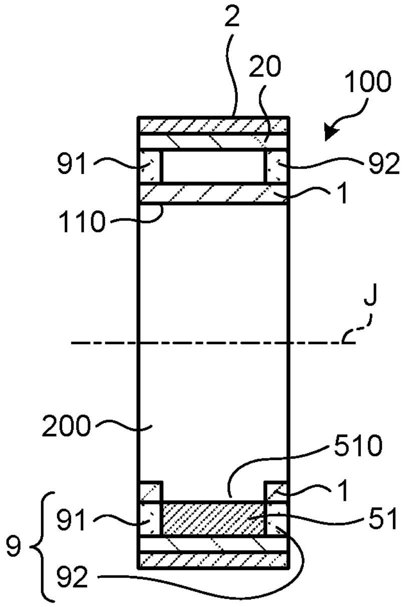
FIG. 4 is a sectional view taken along line Y-Y' in FIG. 2.

FIG. 2 is an internal view of a structure of the detection device 100 in FIG. 1. FIG. 2 is a sectional view of the detection device 100 in FIG. 1 taken along a plane orthogonal to a center line J passing through the center of the hollow 200. FIG. 2 illustrates the section of the detection device 100 taken along a plane passing through the midpoint in a length direction of the outer electrode 2 along the center line J. FIG. 3 is a sectional view taken along line X-X' in FIG. 2. FIG. 4 is a sectional view taken along line Y-Y' in FIG. 2.

In FIG. 2, the detection device 100 includes a temperature sensor 3, an acceleration sensor 4, an LED driver 5, a light sensor 6, a short-distance wireless communication driver 7, a battery 8, a coil 9, a control circuit 10, a red light emitting diode (LED) 51, a near-infrared LED 52, and a green LED 53. These components are provided outside the inner electrode 1 and inside the outer electrode 2, in other words, between the inner electrode 1 and the outer electrode 2. The components are mounted on a flexible substrate 20. The components can mutually communicate signals through the flexible substrate 20.

The red LED 51 emits red light. The near-infrared LED 52 emits near-infrared light. The green LED 53 emits green light. In other words, the detection device 100 includes light sources provided outside the inner electrode 1 and inside the outer electrode 2 (between the inner electrode 1 and the outer electrode 2). The LED driver 5 drives the red LED 51, the near-infrared LED 52, and the green LED 53 to emit light.

The inner electrode 1 includes openings 510, 520, and 530. The opening 510 is provided in the inner surface 110 of the inner electrode 1, at a position corresponding to the red LED 51. As understood from FIGS. 2 and 4, the opening 510 is provided at a position through which the red LED 51 faces the hollow 200. Red light emitted by the red LED 51 passes through the opening 510 and is emitted toward the hollow 200. The red light emitted by the red LED 51 is incident on a finger inserted in the hollow 200. Thus, the red LED 51 is a light source configured to irradiate a finger with red light.

The opening 520 is provided in the inner surface 110 of the inner electrode 1, at a position corresponding to the near-infrared LED 52. The opening 520 is provided at a position through which the near-infrared LED 52 faces the hollow 200. Near-infrared light emitted by the near-infrared LED 52 passes through the opening 520 and is emitted toward the hollow 200. The near-infrared light emitted by the near-infrared LED 52 is incident on a finger inserted in the hollow 200. Thus, the near-infrared LED 52 is a light source configured to irradiate a finger with near-infrared light.

The opening 530 is provided in the inner surface 110 of the inner electrode 1, at a position corresponding to the green LED 53. The opening 530 is provided at a position through which the green LED 53 faces the hollow 200. Green light emitted by the green LED 53 passes through the opening 530 and is emitted toward the hollow 200. The green light emitted by the green LED 53 is incident on a finger inserted in the hollow 200. Thus, the green LED 53 is a light source configured to irradiate a finger with green light.

The inner electrode 1 also has the opening 60. The opening 60 is provided in the inner surface 110 of the inner electrode 1, at a position corresponding to the light sensor 6. The opening 60 is provided at a position through which the hollow 200 faces the light sensor 6. The light sensor 6 detects light passing through the opening 60. With the light sensor 6, it is possible to measure change in the intensity of the light.

The light sensor 6 receives light emitted from the red LED 51, the near-infrared LED 52, and the green LED 53 and passing through a finger inserted in the hollow 200. The light sensor 6 detects change in the intensity of the received light. The light sensor 6 is, for example, an organic photodiode (OPD) and outputs an electric signal in accordance with incident light.

When the red LED 51 is on but the near-infrared LED 52 and the green LED 53 are not on, red light passing through the finger is input to the light sensor 6. When the near-infrared LED 52 is on but the red LED 51 and the green LED 53 are not on, near-infrared light passing through the finger is input to the light sensor 6. When the green LED 53 is on but the red LED 51 and the near-infrared LED 52 are not on, green light passing through the finger is input to the light sensor 6.

The temperature sensor 3 detects the temperature of the inner electrode 1. The inner electrode 1 contacts a finger inserted in the hollow 200. Thus, in other words, the temperature sensor 3 detects the temperature of the finger through the inner electrode 1. The temperature sensor 3 and the inner electrode 1 are preferably covered by a member (hereinafter referred to as a heat insulating member) having a heat insulating property to avoid influence on the value of the temperature of the inner electrode 1 detected by the temperature sensor 3. In the present example, the heat insulating member is the flexible substrate 20. The temperature sensor 3 and the inner electrode 1 are preferably covered by providing the heat insulating member outside the inner electrode 1 and inside the outer electrode 2 (between the inner electrode 1 and the outer electrode 2).

The acceleration sensor 4 detects acceleration applied to the detection device 100. A detected value of the acceleration applied to the detection device 100 is used to remove influence of body motion of a person wearing the detection device 100 as described later.

The short-distance wireless communication driver 7 includes a non-illustrated antenna. The short-distance wireless communication driver 7 communicates signals between the detection device 100 and another device. The short-distance wireless communication driver 7 can transmit, for example, data measured by each component of the detection device 100 to another device. In addition, the short-distance wireless communication driver 7 can receive, for example, data transmitted by another device.

The battery 8 supplies electric power to each component of the detection device 100. The battery 8 is, for example, a lithium ion battery. A battery driver 81 controls the battery 8. The battery 8 is charged by the battery driver 81.

The coil 9 is a charging coil for charging the battery 8. The coil 9 includes a winding wire wound around the outer periphery of the inner electrode 1 outside the inner electrode 1 and inside the outer electrode 2 (between the inner electrode 1 and the outer electrode 2). An induced current flows through the coil 9 based on an applied magnetic field as described later. The coil 9 includes a coil 91 and a coil 92. As illustrated in FIGS. 3 and 4, the coils 91 and 92 are each wound around the outer peripheral surface of the inner electrode 1. The coil 91 is provided on one end side of the outer electrode 2 along the center line J, and the coil 92 is provided on the other end side of the outer electrode 2 along the center line J. The coils 91 and 92 are coupled in parallel to the battery driver 81. Therefore, the battery 8 can be charged by an induced current flowing through any one of the coils 91 and 92. The winding wires of the coils 91 and 92 are each covered and insulated.

The control circuit 10 controls each component of the detection device 100. The control circuit 10 is an integrated circuit (IC) such as a micro controller. The control circuit 10 may be a programmable logic device (PLD) such as a field programmable gate array (FPGA).

Figure 5:
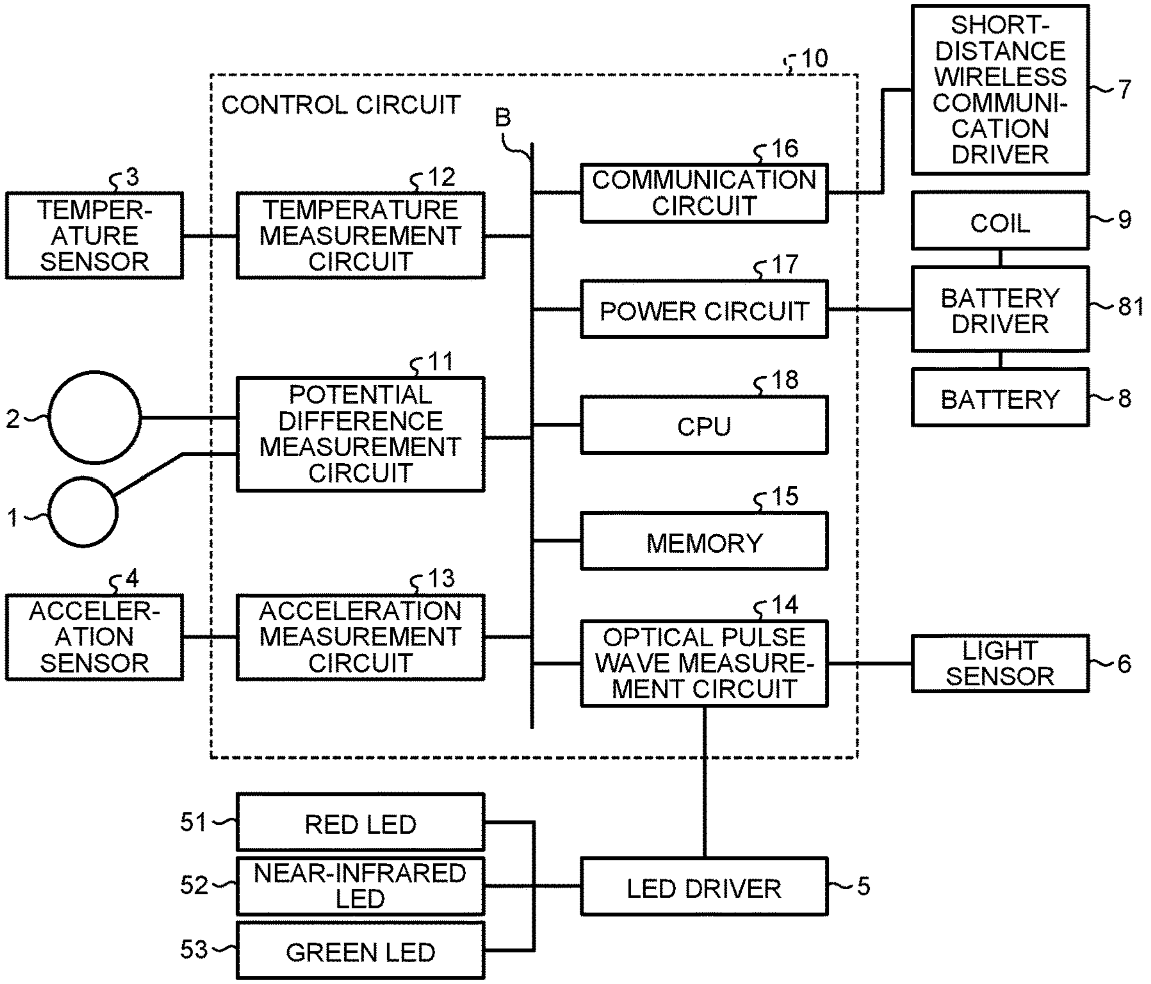
FIG. 5 is a block diagram illustrating an exemplary internal configuration of a control circuit.

FIG. 5 is a block diagram illustrating an exemplary internal configuration of the control circuit 10. As illustrated in FIG. 5, the control circuit 10 of the present example includes a potential difference measurement circuit 11, a temperature measurement circuit 12, an acceleration measurement circuit 13, an optical pulse wave measurement circuit 14, a memory 15, a communication circuit 16, a power circuit 17, and a central processing unit (CPU) 18. These components are coupled to one another through a bus B and can mutually communicate data through the bus B.

The potential difference measurement circuit 11 is coupled to the inner electrode 1 and the outer electrode 2. The potential difference measurement circuit 11 detects the potential difference (in other words, myopotential difference) between the inner electrode 1 and the outer electrode 2.

The temperature measurement circuit 12 is coupled to the temperature sensor 3. The temperature measurement circuit 12 acquires temperature data from the temperature sensor 3.

The acceleration measurement circuit 13 is coupled to the acceleration sensor 4. The acceleration measurement circuit 13 acquires acceleration data from the acceleration sensor 4.

The optical pulse wave measurement circuit 14 is coupled to the LED driver 5 and the light sensor 6. The optical pulse wave measurement circuit 14 measures the pulse frequency, the blood oxygen level (blood oxygen concentration), or the like based on detection data from the light sensor 6.

The memory 15 is a storage configured to store various kinds of data. Aspects of the memory 15 may include, for example, a random access memory (RAM), a read only memory (ROM), an electrically erasable programmable read only memory (EEPROM), and the like.

The communication circuit 16 is coupled to the short-distance wireless communication driver 7. The communication circuit 16 transmits a measurement result or the like to an external device. The external device is, for example, a portable terminal owned by the user of the detection device 100, such as a smartphone or a tablet. The portable terminal such as a smartphone or a tablet includes a display screen. When data received from the detection device 100 is displayed on the screen, the user of the detection device 100 can check the data received from the detection device 100.

The power circuit 17 is coupled to the battery driver 81. The power circuit 17 controls charging of the battery 8 and supplies electric power from the battery 8 to each component.

The CPU 18 is a controller configured to control each component in the control circuit 10. The CPU 18 measures or calculates biological information such as the pulse wave velocity, the blood pressure, or the pulse frequency by executing a predetermined computer program.

Detection of Pulse Wave Velocity by Detection Device

Figure 6:
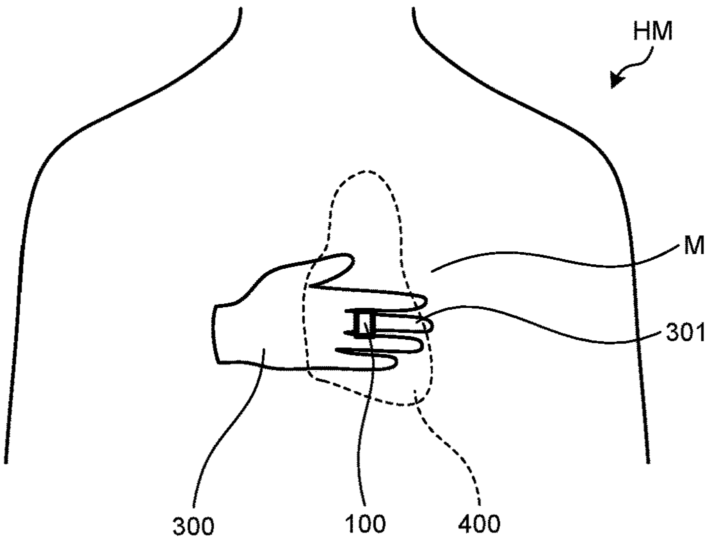
FIG. 6 is a diagram for describing an exemplary method of using the detection device.
Figure 7:
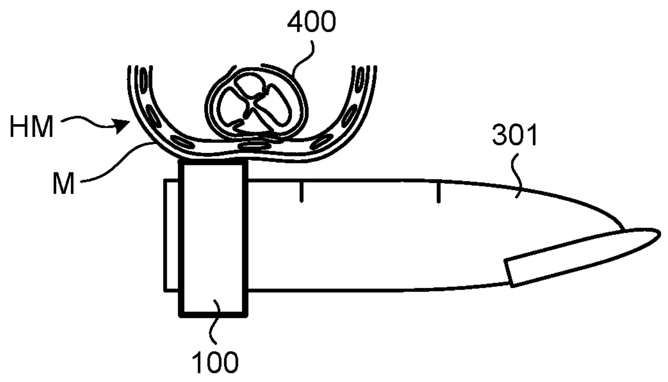
FIG. 7 is a diagram for describing the exemplary method of using the detection device.

FIGS. 6 and 7 are diagrams for describing an exemplary method of using the detection device 100. As illustrated in FIG. 6, a person wearing the detection device 100 on a finger 301 of a hand 300 closely places the hand 300 on the body surface of a chest M of the person. In this state, the finger 301 is pressed against the body surface so that the detection device 100 is positioned on the body surface near a heart 400 in the chest M of a human body HM.

Figure 8:
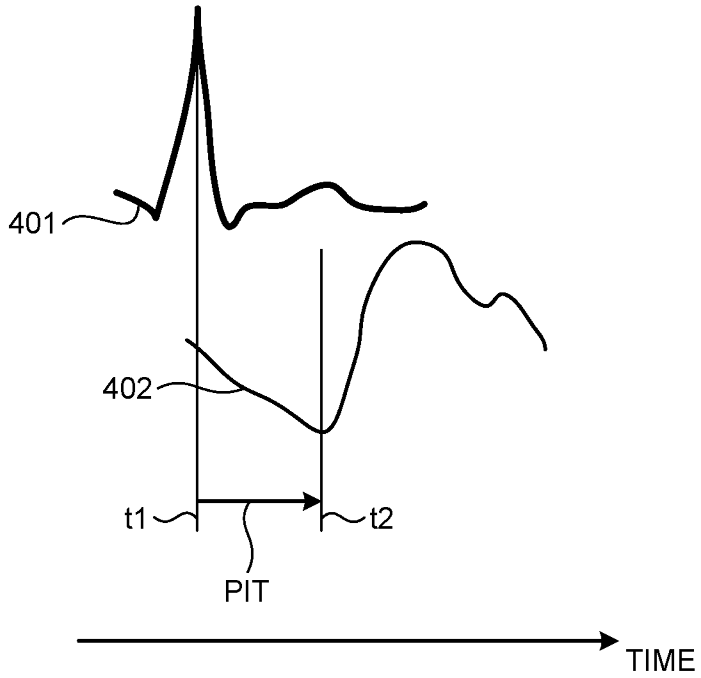
FIG. 8 is a waveform chart for describing a method of calculating pulse wave velocity.

FIG. 8 is a waveform chart for describing processing of calculating the pulse wave velocity. FIG. 8 illustrates an electrocardiogram waveform 401 and a pulse wave waveform 402. The light volume pulse wave (Photoplethysmogram) of the pulse wave waveform 402 delays relative to the peak value of the electrocardiogram waveform 401. A pulse wave velocity PWV is obtained by dividing the distance from the heart to the finger, in other words, a distance L to the detection device 100, by a time PIT of the delay.

When the distance L from the heart to the detection device 100 is stored in advance, the pulse wave velocity PWV can be calculated by measuring the time PIT. Specifically, the pulse wave velocity PWV is given by "the distance L/the time PIT". It is possible to easily measure the pulse wave velocity PWV at all times by using the detection device 100. The pulse wave velocity PWV increases as arteriosclerosis advances, and thus it is possible to find high blood pressure early by continually measuring the pulse wave velocity PWV with the detection device 100. For example, an approximate value of the distance L may be set in advance and stored in the above-described memory 15.

Charging of Battery

Figure 9:
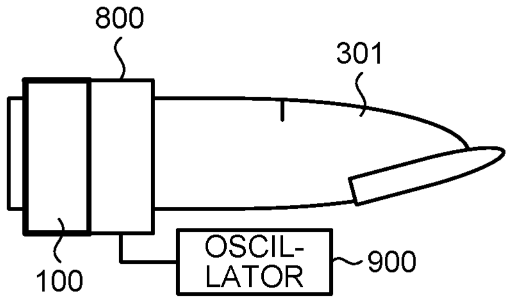
FIG. 9 is a diagram for describing a method of charging the detection device.

FIG. 9 is a diagram for describing a method of charging the detection device 100. As illustrated in FIG. 9, a charging adapter 800 is additionally worn on the finger 301 while the detection device 100 is worn on the finger 301. The charging adapter 800 has a circular ring shape, and the finger 301 is inserted into a hollow thereof. Then, as illustrated in FIG. 9, the detection device 100 and the charging adapter 800 are moved closer to each other while being worn on the finger 301. An oscillator 900 is coupled to the charging adapter 800. The oscillator 900 outputs an oscillation signal a current value of which changes in a predetermined period.

Figure 10:
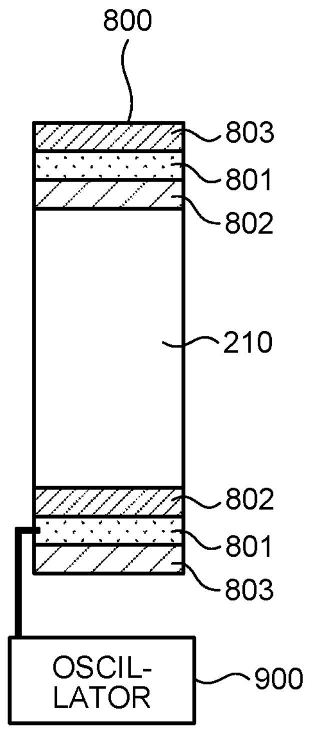
FIG. 10 is a schematic view illustrating an exemplary charging adapter.

FIG. 10 is a schematic view illustrating an example of the charging adapter 800. As illustrated in FIG. 10, the charging adapter 800 includes a charging coil 801, an inner annular part 802, and an outer annular part 803. The charging coil 801 is provided outside the inner annular part 802 and inside the outer annular part 803. In other words, the charging coil 801 is provided between the inner annular part 802 and the outer annular part 803. The inner annular part 802 has substantially the same shape as that of the inner electrode 1 of the detection device 100. The outer annular part 803 has substantially the same shape as that of the outer electrode 2 of the detection device 100. A hollow 210 inside the inner annular part 802 is a part into which the finger is inserted. When the finger wearing the detection device 100 is inserted into the hollow 210, the detection device 100 and the charging adapter 800 are worn on the finger 301 as illustrated in FIG. 9.

When the detection device 100 and the charging adapter 800 are worn on the finger 301, a winding wire of the charging coil 801 is wound coaxially with the inner electrode 1 of the detection device 100. In this state, a magnetic field of the coil 801 changes when the oscillation signal from the oscillator 900 is provided to the coil 801. With electromagnetic induction due to the change in the magnetic field of the coil 801, a magnetic field applied to the coil 9 in the detection device 100 changes and an induced current flows through the coil 9. Thus, the battery driver 81 is operated by the induced current flowing through the coil 9 in the detection device 100, and the battery 8 is charged. Thus, the coil 9 in the detection device 100 can charge the battery 8 based on the applied magnetic field.

As described above with reference to FIGS. 3 and 4, the coil 9 in the detection device 100 includes the coil 91 as a first coil and the coil 92 as a second coil. The coils 91 and 92 are provided on opposite sides in a direction in which a finger is inserted into the hollow 200 of the detection device 100. With this configuration, when the detection device 100 and the charging adapter 800 are worn on the finger 301 as illustrated in FIG. 9, the charging adapter 800 is positioned close to the coil 91 or 92 irrespective of the wearing orientation of the detection device 100 and the charging adapter 800 on the finger. Thus, the charging adapter 800 can be worn on the finger 301 without attention to the wearing orientation of the charging adapter 800. When the coil 91 or 92 is positioned close to the charging adapter 800, an induced current efficiently flows through the coil 91 or 92 due to a magnetic field generated by the charging adapter 800. Thus, it is possible to easily charge the battery 8 of the detection device 100 by wearing the charging adapter 800 on the finger 301 without attention to the wearing orientation. Whether the detection device 100 is worn on a right-hand finger or a left-hand finger, it is possible to charge the battery 8 of the detection device 100 by wearing the charging adapter 800 on this finger 301.

Another Method of Using Detection Device

Figure 11:
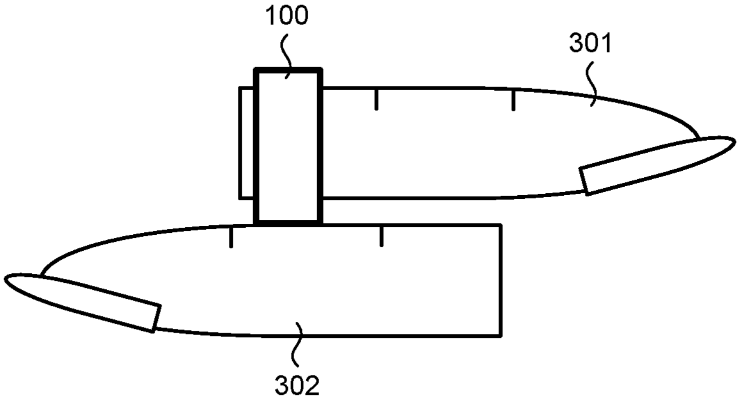
FIG. 11 is a diagram illustrating another method of using the detection device.

FIG. 11 is a diagram illustrating another method of using the detection device 100. As illustrated in FIG. 11, the detection device 100 is worn on the finger 301. In this state, the detection device 100 is closely placed on a finger 302 of the opposite hand of the same person. For example, in a case in which the finger 301 is the middle finger of the left hand, the finger 302 is a finger of the right hand of the same person. Then, the surface of the outer electrode 2 of the detection device 100 is pressed against the surface of the finger 302. Thus, the pulse wave velocity can be calculated as described above with reference to FIG. 8. The state illustrated in FIG. 11 is a measurement state similar to a lead I electrocardiogram measurement method.

Figure 12:
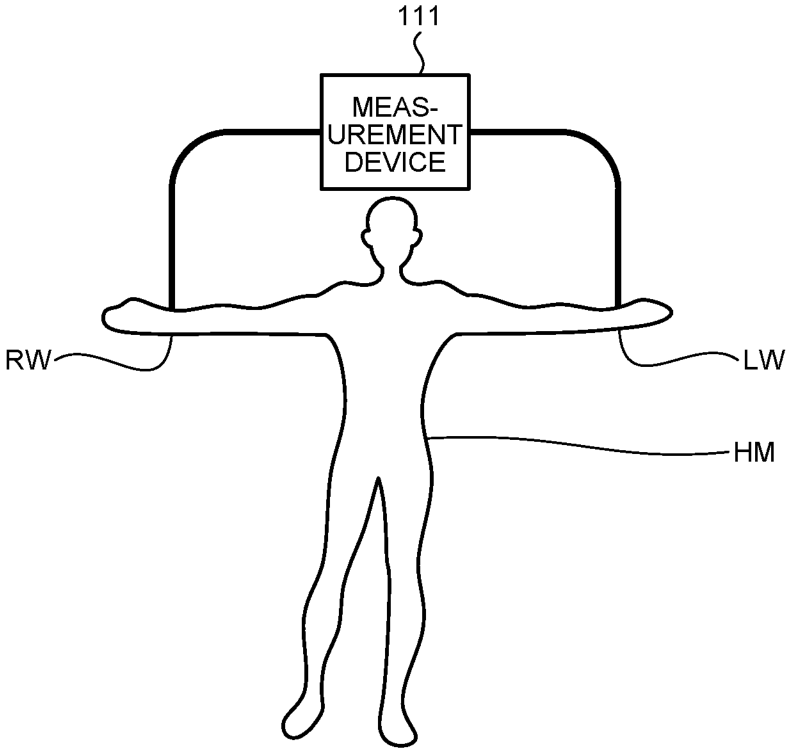
FIG. 12 is a diagram for describing a lead I electrocardiogram measurement method.
Figure 13:
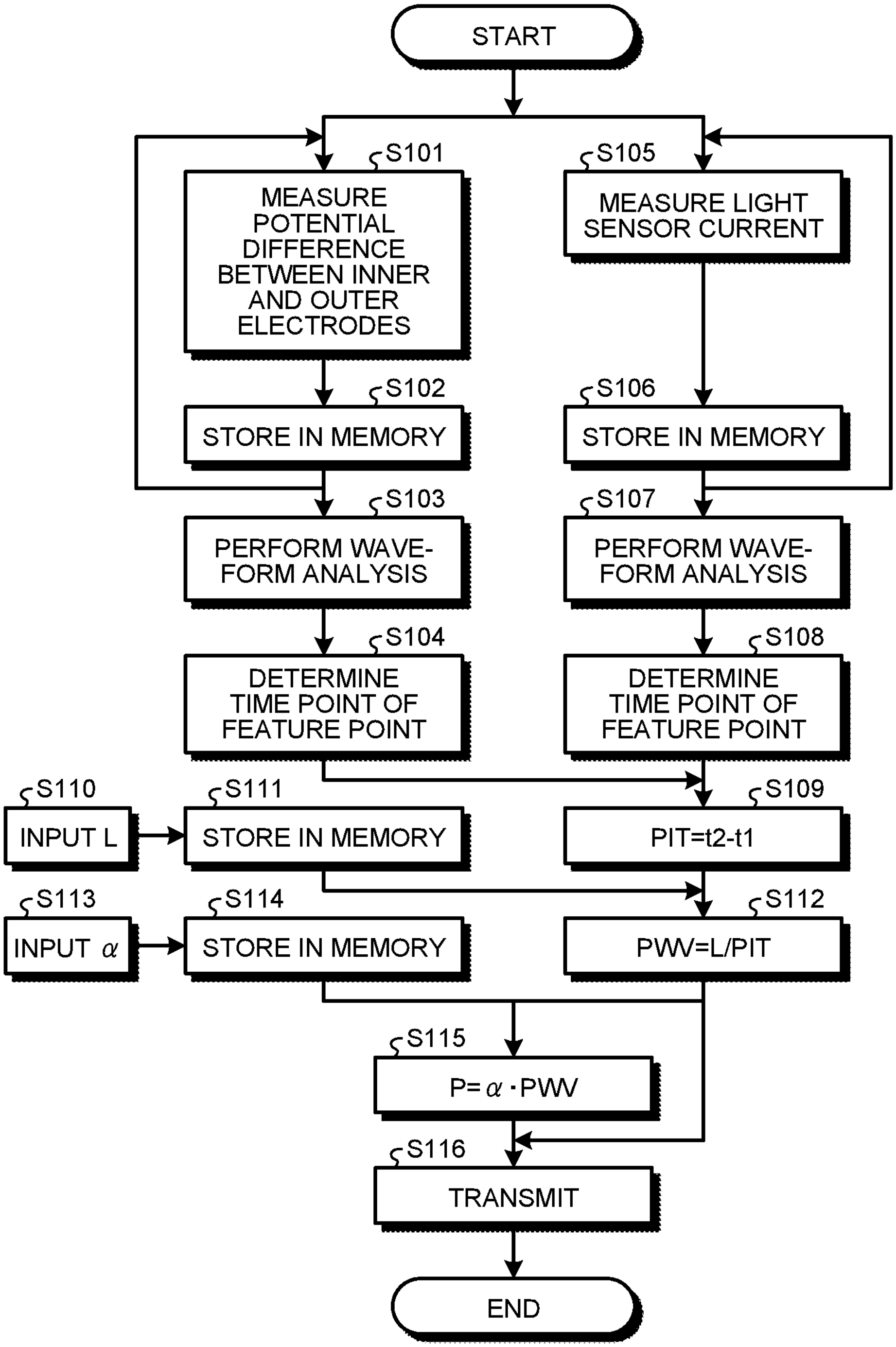
FIG. 13 is a flowchart illustrating processing of measuring pulse wave velocity and blood pressure by the detection device.

FIG. 12 is a diagram for describing the lead I electrocardiogram measurement method. As illustrated in FIG. 12, the lead I electrocardiogram measurement method is a method of attaching electrodes on a right wrist RW and a left wrist LW, respectively, of the human body HM and obtaining an electrocardiogram by a measurement device 111. Thus, the other method of using the detection device 100, which is illustrated in FIG. 11, is a measurement method similar to the lead I electrocardiogram measurement method. In FIG. 11, the detection device 100 may be brought into intimate contact with a wrist instead of the finger 302. Measurement of pulse wave velocity and blood pressure FIG. 13 is a flowchart illustrating processing of measuring the pulse wave velocity and the blood pressure by the detection device 100. In FIG. 13, the above-described potential difference measurement circuit 11 measures the potential difference between the inner electrode 1 and the outer electrode 2 (step S101). The measured potential difference has a periodic waveform. A result of the potential difference measurement at step S101 is stored in the memory 15 (step S102). The processing at step S101 and the processing at step S102 are repeatedly performed. The measurement result stored in the memory 15 is subjected to waveform analysis by the control circuit 10 (step S103), and the time point of a feature point is determined (step S104). In this example, a time point (referred to as a time point t1) corresponding to a peak value that is a feature point of the above-described electrocardiogram waveform 401 (refer to FIG. 8) is determined.

In addition, the above-described optical pulse wave measurement circuit 14 turns on the green LED 53 and measures an output current value of the light sensor 6 (step S105). The measured output current value has a periodic waveform. A result of the output current value measurement at step S105 is stored in the memory 15 (step S106). The processing at step S105 and the processing at step S106 are repeatedly performed. The measurement result stored in the memory 15 is subjected to waveform analysis by the control circuit 10 (step S107) and, the time point of a feature point is determined (step S108). In this example, the time point (referred to as time point t2) of a lower limit value of the light volume pulse wave (Photoplethysmogram) of the above-described pulse wave waveform 402 (refer to FIG. 8) is determined.

Subsequently, the control circuit 10 calculates the time PIT that is the difference between the two time points (step S109). Specifically, the time PIT is given by "the time point t2—the time point t1".

The above-described distance L is input in advance or is set in advance (step S110) and stored in the memory 15 (step S111). The pulse wave velocity PWV is calculated by dividing the distance L by the time PIT (step S112). Specifically, the pulse wave velocity PWV is given by "the distance L/the time PIT".

Subsequently, blood pressure P is calculated. A proportional coefficient α for calculating the blood pressure P is input in advance (step S113) and stored in the memory 15 (step S114). The proportional coefficient α is calculated by measuring the blood pressure with another measurement device in advance.

Since the blood pressure P is proportional to the pulse wave velocity PWV, the blood pressure P is calculated by multiplying the pulse wave velocity PWV by the proportional coefficient α (step S115). Specifically, the blood pressure P is given by "the proportional coefficient α× the pulse wave velocity PWV".

The pulse wave velocity PWV and the blood pressure P obtained through the above-described processing are transmitted to another device by the communication circuit 16 and the short-distance wireless communication driver 7 (step S116). The pulse wave velocity PWV and the blood pressure P are transmitted to, for example, a smartphone. The transmission from the detection device 100 to the other device is performed by short-distance wireless communication in the present example.

Instead of turning on the green LED 53 as a green light source at step S105, the red LED 51 as a red light source or the near-infrared LED 52 as a near-infrared light source may be turned on to measure the output current value of the light sensor 6.

Measurement of Respiratory Rate

Figure 14:
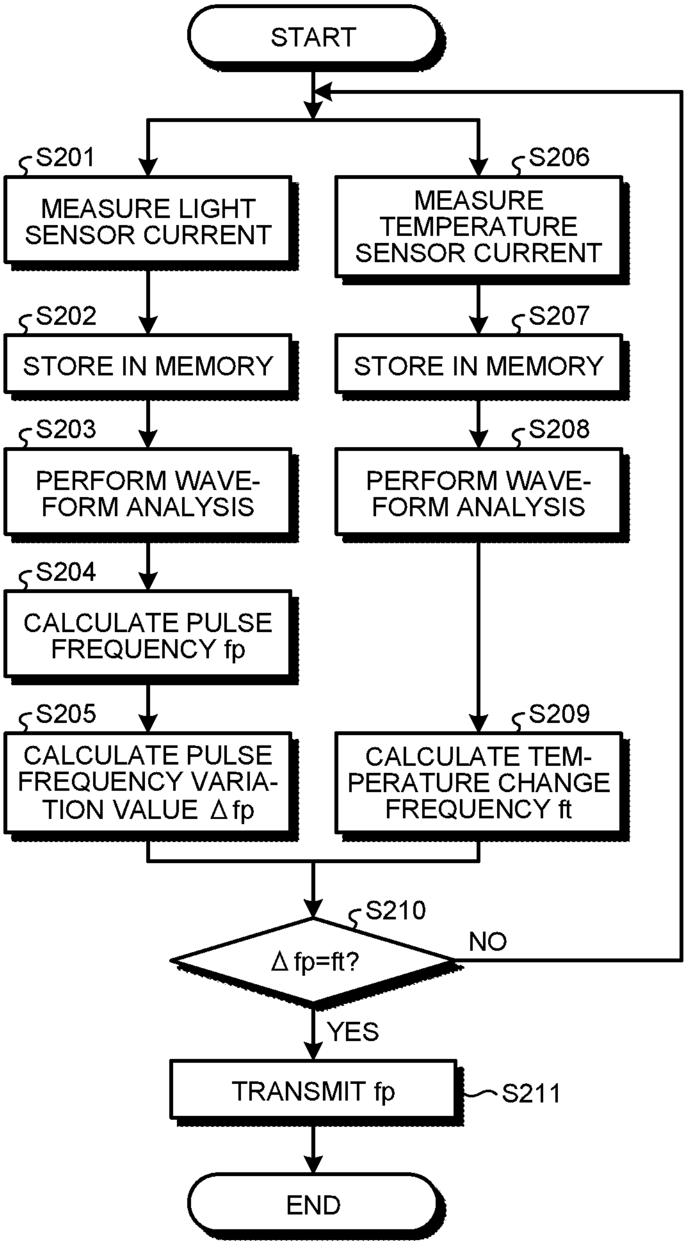
FIG. 14 is a flowchart illustrating processing of measuring a respiratory rate by the detection device.

FIG. 14 is a flowchart illustrating processing of measuring the respiratory rate by the detection device 100. In FIG. 14, the above-described optical pulse wave measurement circuit 14 turns on the green LED 53 and measures the output current value of the light sensor 6 (step S201). The measured output current value has a periodic waveform. A result of the output current value measurement at step S201 is stored in the memory 15 (step S202). The measurement result stored in the memory 15 is subjected to waveform analysis by the control circuit 10 (step S203), a pulse frequency fp is calculated from the period of a feature point (step S204), and in addition, a pulse frequency variation value Δfp as the variation value of the pulse frequency fp is calculated (step S205). The pulse frequency variation value Δfp as the variation value of the pulse frequency fp can be assumed to be the respiratory rate.

Processing described below is performed in parallel with the processing at steps S201 to S205. The above-described temperature measurement circuit 12 measures a current value as temperature data from the temperature sensor 3 (step S206). A result of the current value measurement at step S206 is stored in the memory 15 (step S207). The measurement result stored in the memory 15 is subjected to waveform analysis by the control circuit 10 (step S208), and a temperature change frequency ft is calculated (step S209).

Subsequently, whether the pulse frequency variation value Δfp calculated at step S205 matches the temperature change frequency ft calculated at step S209 is determined (step S210). In a case in which the pulse frequency variation value Δfp matches the temperature change frequency ft at step S210 (Yes at step S210), the pulse frequency variation value Δfp is determined as the respiratory rate. In this case, the pulse frequency fp is transmitted to another device by the communication circuit 16 and the short-distance wireless communication driver 7 (step S211). The pulse frequency fp is transmitted to, for example, a smartphone. The transmission from the detection device 100 to the other device is performed by short-distance wireless communication in the present example. The case in which the pulse frequency variation value Δfp matches the temperature change frequency ft is a case in which their difference falls in a range determined in advance, in other words, a predetermined range.

In a case in which the pulse frequency fp does not match the temperature change frequency ft at step S210 (No at step S210), in other words, a case in which their difference does not fall in the predetermined range, the pulse frequency fp is not transmitted from the detection device 100 to another device. Specifically, in the case in which their difference does not have a value in the predetermined range, it is determined that the pulse frequency variation value Δfp is not the respiratory rate, and the pulse frequency fp is not transmitted to another device. In this case, processing returns to steps S201 and S206 and is continued therefrom.

Instead of turning on the green LED 53 as a green light source at step S201, the red LED 51 as a red light source or the near-infrared LED 52 as a near-infrared light source may be turned on to measure the output current value of the light sensor 6.

Processing of Removing Body Motion Noise

Figure 15:
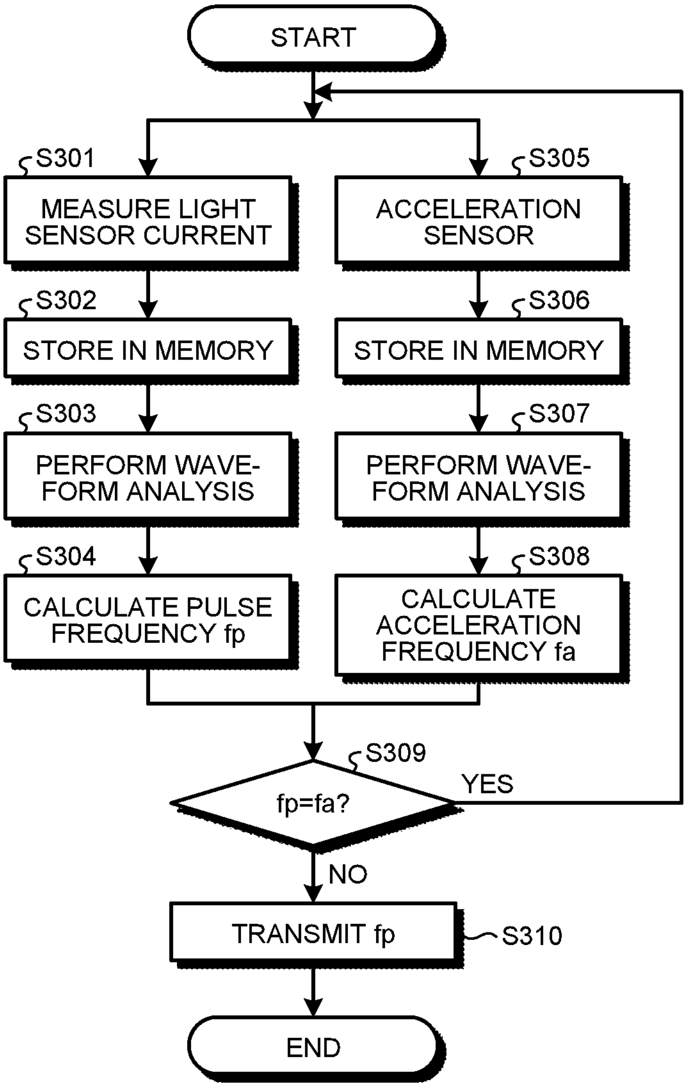
FIG. 15 is a flowchart illustrating processing of removing body motion noise.

FIG. 15 is a flowchart illustrating a method of removing body motion noise. In FIG. 15, the above-described optical pulse wave measurement circuit 14 turns on the green LED 53 and measures an output current of the light sensor 6 (step S301). A result of the output current measurement at step S301 is stored in the memory 15 (step S302). The measurement result stored in the memory 15 is subjected to waveform analysis by the control circuit 10 (step S303), and the pulse frequency fp is calculated (step S304).

Processing described below is performed in parallel with the processing at steps S301 to S304. The acceleration measurement circuit 13 stores the waveform of acceleration detected by the acceleration sensor 4 in the memory 15 (steps S305 and S306). The acceleration waveform stored in the memory 15 is subjected to waveform analysis by the control circuit 10 (step S307), and a frequency fa of change in the acceleration is calculated (step S308).

Subsequently, whether the pulse frequency fp calculated at step S304 matches the frequency fa of change in the acceleration calculated at step S308 is determined (step S309). In a case in which the pulse frequency fp does not match the frequency fa at step S309 (No at step S309), the pulse frequency fp is transmitted to another device by the communication circuit 16 and the short-distance wireless communication driver 7 (step S310). Specifically, in the case in which the pulse frequency fp does not match the frequency fa, it is considered that the calculated value is not body motion noise. Thus, the calculated value is transmitted as the pulse frequency fp to the other device. For example, the pulse frequency fp is transmitted to, for example, a smartphone. The transmission from the detection device 100 to the other device is performed by short-distance wireless communication in the present example. The case in which the pulse frequency fp does not match the frequency fa is a case in which their difference does not fall in a range determined in advance, in other words, a predetermined range.

In a case in which the pulse frequency fp matches the frequency fa at step S309 (Yes at step S309), the calculated value is considered to be body motion noise and thus the pulse frequency fp is not transmitted to another device. In other words, in a case in which their difference falls in the predetermined range, the pulse frequency fp is not transmitted to another device. Thus, body motion noise is removed. In this case, processing returns to steps S301 and S305 and is continued therefrom to perform measurement again.

Instead of turning on the green LED 53 as a green light source at step S301, the red LED 51 as a red light source or the near-infrared LED 52 as a near-infrared light source may be turned on to measure the output current value of the light sensor 6.

Method of Measuring Blood Oxygen Level (Blood Oxygen Concentration)

The blood oxygen level (blood oxygen concentration) (hereinafter referred to as SpO2) as biological information can be acquired by measuring light transmitting through a living body such as a finger. For example, SpO2 can be measured based on Expression (1) below.

$$SpO2=b-a\cdot R \tag{1}$$

As in Expression (1) described above, SpO2 is a linear function of the value R. In Expression (1) described above, "a" and "b" are predetermined coefficients. The value R in Expression (1) is defined by Expression (2) below.

$$R=(ACr/DCr)/(\mathrm{ACir}/\mathrm{DCir}) \tag{2}$$

In Expression (2) described above, ACr represents an alternating-current component of a measured value of red light (Red), DCr represents a direct-current component of the measured value of red light, ACir represents an alternating-current component of a measured value of near-infrared light (IR), and DCir represents a direct-current component of the measured value of near-infrared light. An alternating-current component is a component of a pulse wave that appears in direct current. SpO2 that is a linear function of the value R is calibrated with oxygen concentration in blood collected in advance.

Figure 16:
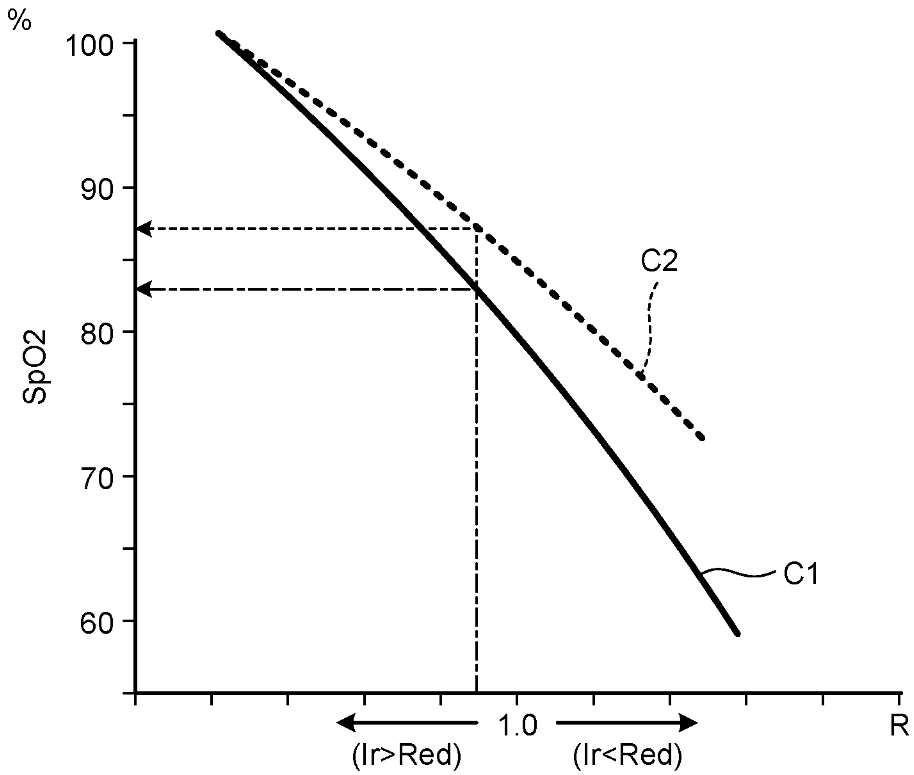
FIG. 16 is a graph illustrating an exemplary value of SpO2.

More specifically, the value of SpO2 can be acquired as follows. Specifically, the value of SpO2 corresponding to the above-described value R is measured in advance, and the value of SpO2 is acquired based on a curve of the measured value. FIG. 16 is a graph illustrating an exemplary value of SpO2. For example, in FIG. 16, the curve of the measured value plots a calculated value for the above-described value R, and the vertical axis represents the value of SpO2. The value R is smaller than 1.0 when "Ir" light is larger than "Red" light (Ir>Red), and the value R is larger than 1.0 when "Red" light is larger than "Ir" light (Ir<Red).

As illustrated in FIG. 16, when the above-described value R is calculated, the value of SpO2 corresponding to the value R can be acquired. For example, when a curve C1 in FIG. 16 is used, the value of SpO2 can be acquired as approximately 83% for the value R of 0.9. For example, when a curve C2 in FIG. 16 is used, the value of SpO2 can be acquired as approximately 87% for the value R of 0.9.

Moreover, when the above-described coefficients "a" and "b" are determined to obtain an approximate expression of the curve C1 or C2, the value of SpO2 can be acquired by using Expression (1).

Figure 17:
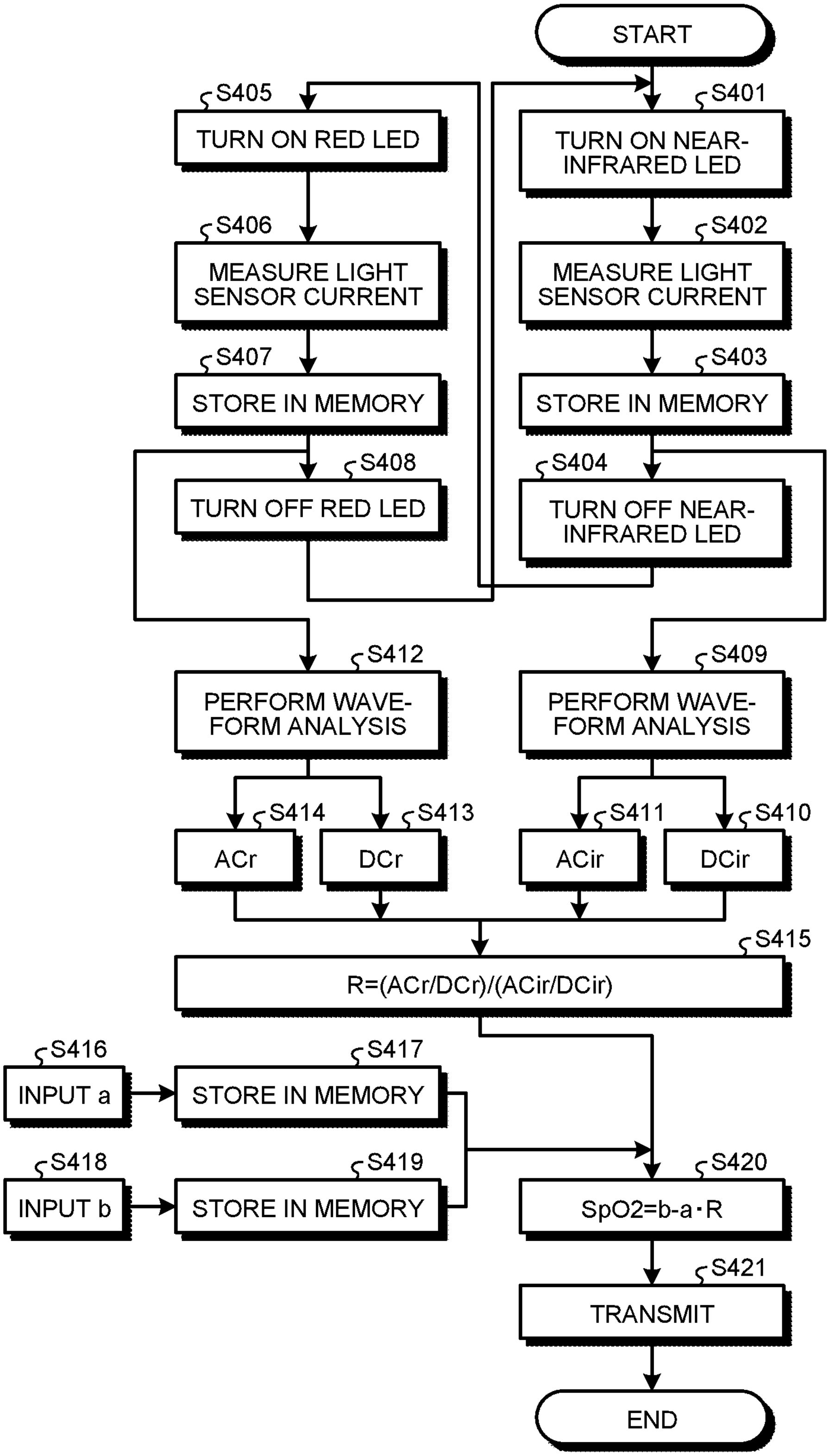
FIG. 17 is a flowchart illustrating processing of measuring blood oxygen level (blood oxygen concentration) by the detection device.

FIG. 17 is a flowchart illustrating a method of measuring the blood oxygen level (blood oxygen concentration) by the detection device 100. In FIG. 17, the optical pulse wave measurement circuit 14 causes the LED driver 5 to turn on the near-infrared LED 52 (step S401). The optical pulse wave measurement circuit 14 measures an output current of the light sensor 6 (step S402). A result of the current value measurement at step S402 is stored in the memory 15 (step S403). The optical pulse wave measurement circuit 14 causes the LED driver 5 to turn off the near-infrared LED 52 (step S404).

Then, the optical pulse wave measurement circuit 14 causes the LED driver 5 to turn on the red LED 51 (step S405). The optical pulse wave measurement circuit 14 measures an output current of the light sensor 6 (step S406). A result of the current value measurement at step S406 is stored in the memory 15 (step S407). The optical pulse wave measurement circuit 14 causes the LED driver 5 to turn off the red LED 51 (step S408). Processing returns to step S401, and the optical pulse wave measurement circuit 14 repeats the above-described processing. Specifically, the optical pulse wave measurement circuit 14 alternately turns on the red LED 51 and the near-infrared LED 52, repeatedly measures light sensor current with the light sensor 6, and stores the measured current in the memory 15.

The measurement result of the output current of the light sensor 6 upon the turning-on of the near-infrared LED 52, which is stored in the memory 15, is subjected to waveform analysis by the control circuit 10 (step S409). Through the waveform analysis, the average value (DCir) and amplitude (ACir) of a near-infrared signal waveform are calculated (steps S410 and S411).

In addition, the measurement result of the output current of the light sensor 6 upon the turning-on of the red LED 51, which is stored in the memory 15, is subjected to waveform analysis by the control circuit 10 (step S412). Through the waveform analysis, the average value (DCr) and amplitude (ACr) of a red signal waveform are calculated (steps S413 and S414).

Subsequently, the control circuit 10 calculates the value R for calculating the blood oxygen saturation SpO2 (step S415). The coefficient "a" for calculating the blood oxygen saturation SpO2 is input in advance (step S416) and stored in the memory 15 (step S417). Similarly, the coefficient "b" for calculating the blood oxygen saturation SpO2 is input in advance (step S418) and stored in the memory 15 (step S419). The control circuit 10 calculates the blood oxygen saturation SpO2 based on Expression (1) described above (step S420).

The SpO2 obtained through the above-described processing is transmitted to another device by the communication circuit 16 and the short-distance wireless communication driver 7 (step S421). The SpO2 is transmitted to, for example, a smartphone. The transmission from the detection device 100 to the other device is performed by short-distance wireless communication in the present example.

First Modification

Figure 18:
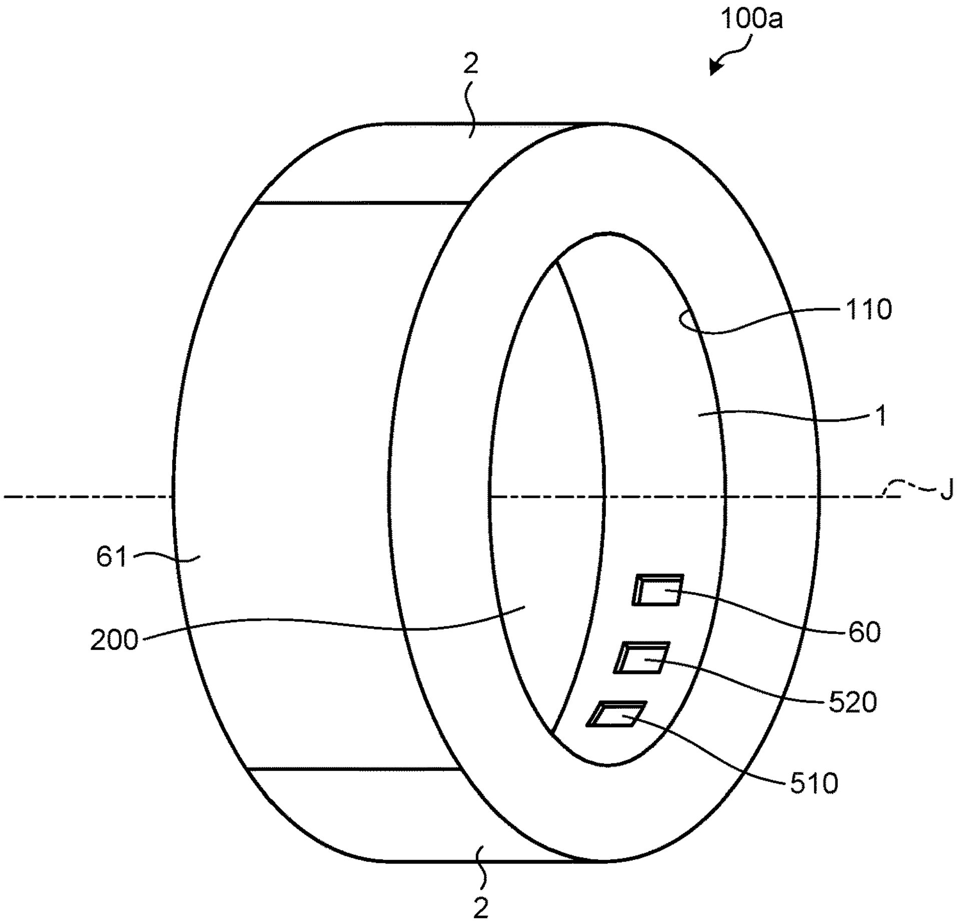
FIG. 18 is an external view of a detection device according to a first modification.
Figure 19:
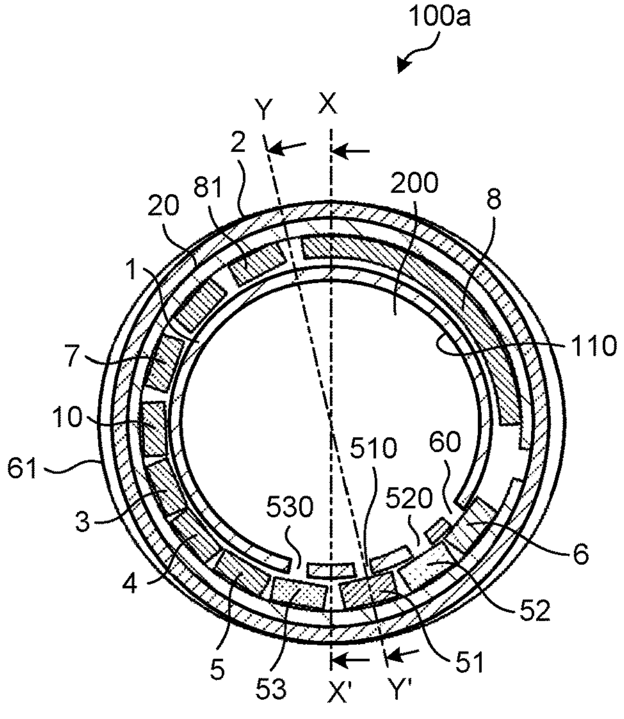
FIG. 19 is an internal view of a structure of the detection device in FIG. 18.
Figure 20:
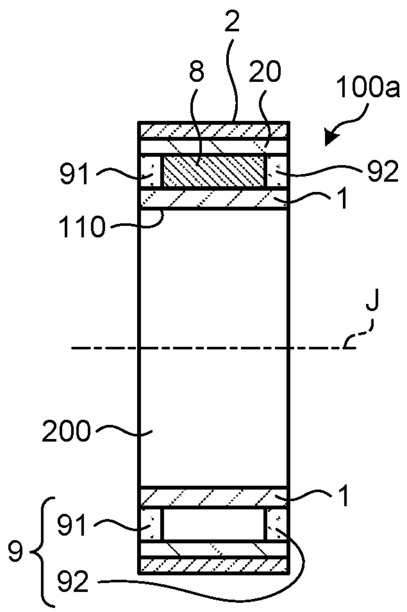
FIG. 20 is a sectional view taken along line X-X' in FIG. 19.
Figure 21:
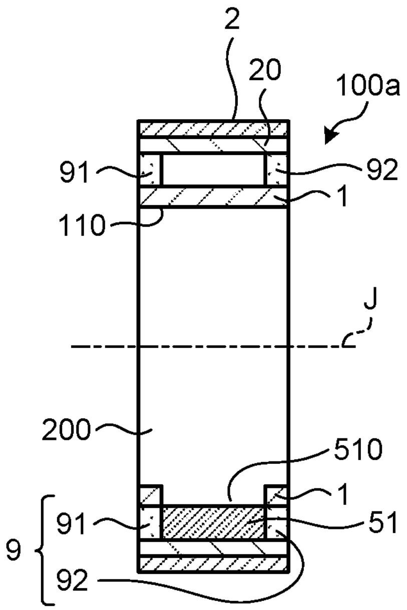
FIG. 21 is a sectional view taken along line Y-Y' in FIG. 19.

FIG. 18 is an external view of a detection device 100*a* according to a first modification. FIG. 19 is an internal view of a structure of the detection device 100*a* in FIG. 18. FIG. 19 is a sectional view of the detection device 100*a* taken along a plane orthogonal to a center line J passing through the center of the hollow 200. FIG. 20 is a sectional view taken along line X-X' in FIG. 19. FIG. 21 is a sectional view taken along line Y-Y' in FIG. 19. In the same manner as the detection device 100, the detection device 100*a* can be worn on a finger.

In FIGS. 18 and 19, the detection device 100*a* includes insulating parts 61 and 62 unlike the detection device 100 described above with reference to FIG. 1. The insulating parts 61 and 62 are provided on the outer surface of the outer electrode 2. With this configuration, on the outer surface of the outer electrode 2, parts not covered by the insulating parts 61 and 62 are exposed and parts covered by the insulating parts 61 and 62 are not exposed. The insulating parts 61 and 62 are provided on opposite sides with the hollow 200 interposed therebetween. The insulating parts 61 and 62 are formed of, for example, resin. The other internal configuration of the detection device 100*a* is the same as the internal configuration of the detection device 100.

As illustrated in FIG. 19, sections of the insulating parts 61 and 62 have elongated crescent shapes. When the detection device 100*a* is worn on a finger, the detection device 100*a* is worn such that the insulating parts 61 and 62 respectively contact two fingers on both sides of the finger on which the detection device 100*a* is worn. For example, when the detection device 100*a* is worn on the middle finger of a right hand, the detection device 100*a* is worn such that the insulating part 61 contacts the forefinger of the same right hand and the insulating part 62 contacts the ring finger of the same right hand. In other words, the insulating part 61 or 62 is provided at a part that another finger (forefinger or ring finger) adjacent to the middle finger of the right hand contacts. Specifically, on the outer surface of the outer electrode 2, the insulating part 61 is provided at a part where another finger adjacent to a finger wearing the detection device 100*a* contacts. On the outer surface of the outer electrode 2, the insulating part 61 is not provided at a part where another finger adjacent to the finger wearing the detection device 100*a* does not contact.

By using the detection device 100*a* with this structure, even if other fingers of the same hand wearing the detection device 100*a* contact the detection device 100*a*, the other fingers of the same hand do not contact the outer electrode 2 of the detection device 100*a* because they are insulated by the insulating parts 61 and 62. Since the other fingers of the same hand do not contact the outer electrode 2 of the detection device 100*a*, it is not necessary to spread the fingers of the hand to avoid finger-to-finger contact during measurement. Thus, when the surface of the outer electrode 2 of the detection device on the finger 301 is pressed against the surface of the finger 302 in the usage described above with reference to FIG. 11, the other fingers of the same hand as that of the finger 301 do not contact the outer electrode 2. Therefore, a guided signal through the finger 301 and the finger 302 of the opposite hand is obtained, and a measurement state approximate to the lead I electrocardiogram measurement method is achieved. As a result, a favorable electrocardiogram is obtained.

Second Modification

Figure 22:
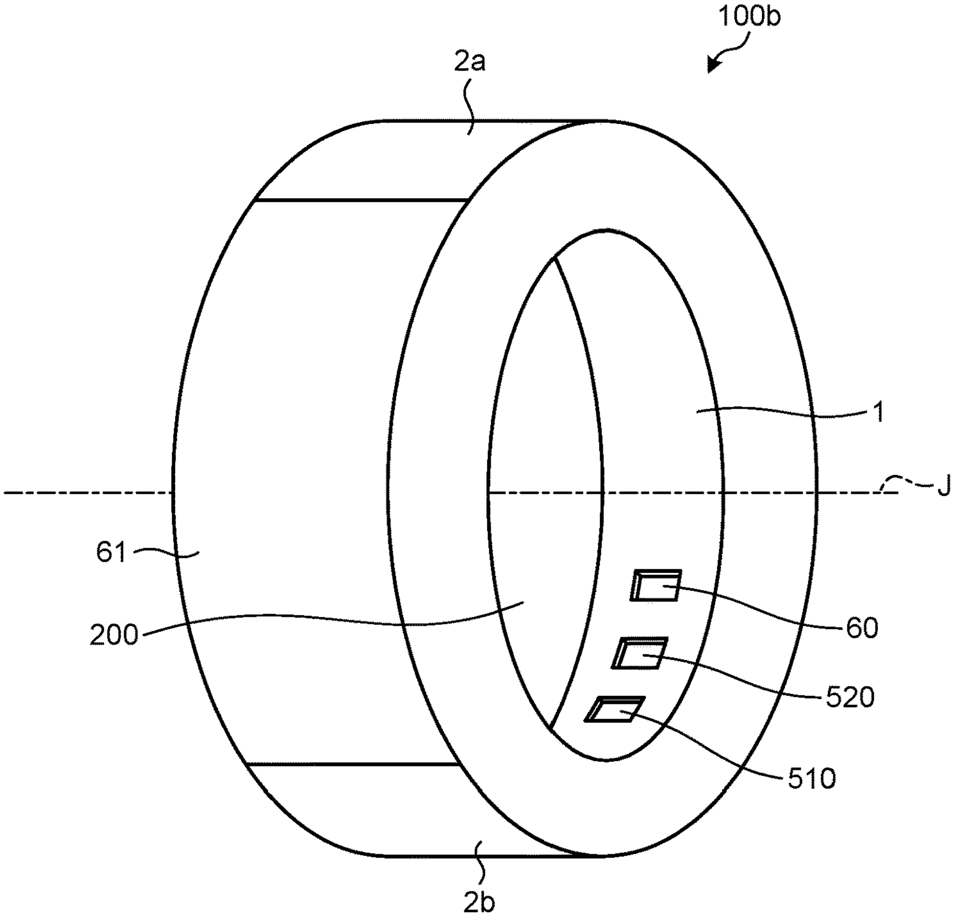
FIG. 22 is an external view of a detection device according to a second modification.
Figure 23:
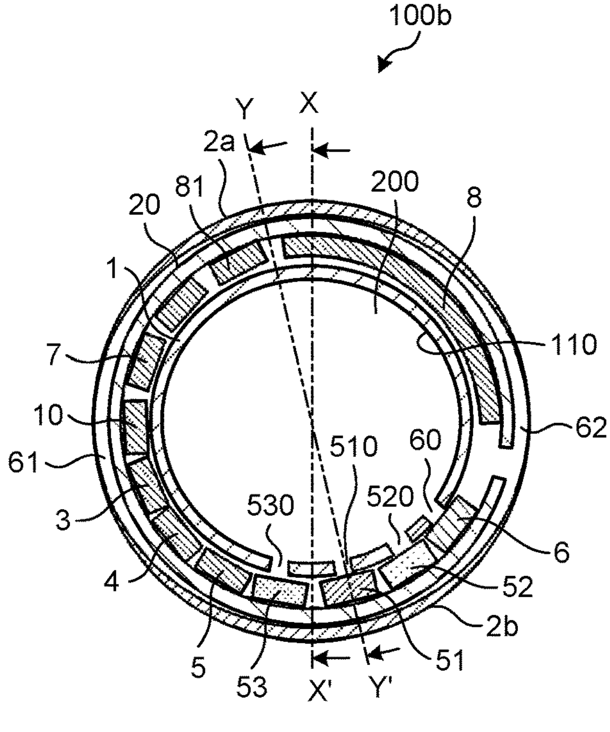
FIG. 23 is an internal view of a structure of the detection device in FIG. 22.
Figure 24:
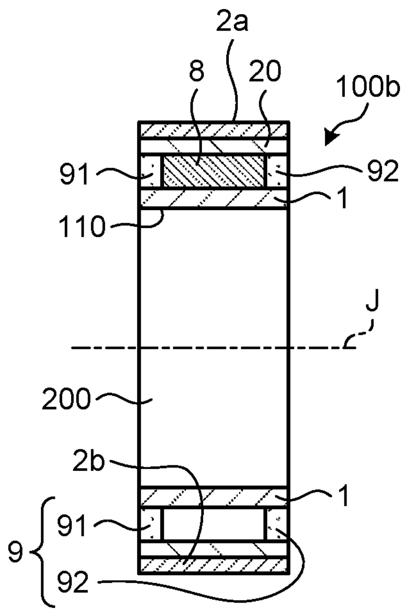
FIG. 24 is a sectional view taken along line X-X' in FIG. 23.
Figure 25:
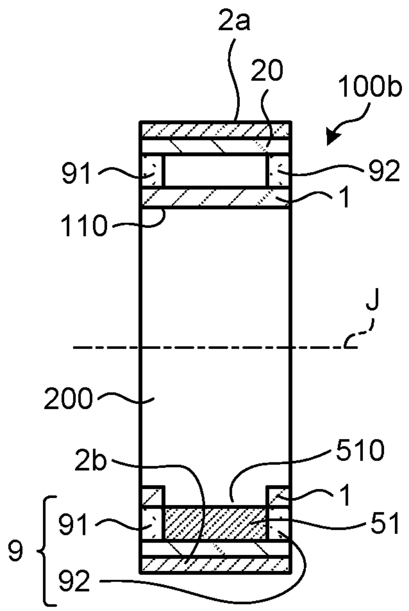
FIG. 25 is a sectional view taken along line Y-Y' in FIG. 23.

FIG. 22 is an external view of a detection device 100*b* according to a second modification. FIG. 23 is an internal view of a structure of the detection device 100*b* in FIG. 22. FIG. 23 is a sectional view of the detection device 100*b* taken along a plane orthogonal to a center line J passing through the center of the hollow 200. FIG. 24 is a sectional view taken along line X-X' in FIG. 23. FIG. 25 is a sectional view taken along line Y-Y' in FIG. 23. In the same manner as the above-described detection devices 100 and 100*a*, the detection device 100*b* can be worn on a finger.

As illustrated in FIGS. 22 to 25, the detection device 100*b* includes divided outer electrodes 2*a* and 2*b*. As illustrated in FIG. 23, the outer electrodes 2*a* and 2*b* are separated from each other such that the outer electrode 2*a* is on the top and the outer electrode 2*b* is on the bottom in the drawing. As illustrated in FIG. 23, the insulating parts 61 and 62 are separated from each other such that the insulating part 61 is on the left side and the insulating part 62 is on the right side in the drawing. With this configuration, on the outer surface of the detection device 100*b*, the outer electrodes 2*a* and 2*b* are exposed at parts not covered by the insulating parts 61 and 62. The other internal configuration of the detection device 100*b* is the same as the internal configurations of the detection devices 100*a* and 100.

With regard to the outer electrode 2*a*, the outer electrode 2*a* is provided between the insulating parts 61 and 62 in the circumferential direction about a center axis along the center line J. The outer electrode 2*a* is provided at a position sandwiched between the insulating parts 61 and 62. With regard to the outer electrode 2*b*, the outer electrode 2*b* is provided between the insulating parts 61 and 62 in the circumferential direction about the center axis along the center line J. The outer electrode 2*b* is provided at a position sandwiched between the insulating parts 61 and 62.

With regard to the insulating part 61, the insulating part 61 is provided between the outer electrodes 2*a* and 2*b* in the circumferential direction about the center axis along the center line J. The insulating part 61 is provided at a position sandwiched between the outer electrodes 2*a* and 2*b*. With regard to the insulating part 62, the insulating part 62 is provided between the outer electrodes 2*a* and 2*b* in the circumferential direction about the center axis along the center line J. The insulating part 62 is provided at a position sandwiched between the outer electrodes 2*a* and 2*b*.

For example, the insulating part 61 or 62 is provided at a part where, when worn on the middle finger of a right hand, the detection device 100*a* contacts another finger (forefinger or ring finger) adjacent to the middle finger. Specifically, on the outer surface of the outer electrode 2, the insulating part 61 or 62 is provided at a part where another finger adjacent to the finger wearing the detection device 100*a* contacts. On the outer surface of the outer electrode 2, the insulating parts 61 and 62 are not provided at a part where another finger adjacent to the finger wearing the detection device 100*a* does not contact.

The outer electrodes 2*a* and 2*b* are each coupled to the potential difference measurement circuit 11. The potential difference measurement circuit 11 measures the potential difference between any one of the outer electrodes 2*a* and 2*b* and the inner electrode 1.

As illustrated in FIG. 23, sections of the insulating parts 61 and 62 have elongated crescent shapes. When the detection device 100*b* is worn on a finger, the detection device 100*b* is worn such that the insulating parts 61 and 62 respectively contact two fingers on both sides of the finger on which the detection device 100*b* is worn.

By wearing the detection device 100*b* in this manner, like the first modification, even if other fingers of the same hand wearing the detection device 100*b* contact the detection device 100*b*, the other fingers of the same hand do not contact the outer electrode 2*a* or 2*b* of the detection device 100*b* because they are insulated by the insulating parts 61 and 62. Since the other fingers of the same hand do not contact the outer electrode 2 of the detection device 100*b*, it is not necessary to spread the fingers of the hand to avoid finger-to-finger contact during measurement. Thus, when the surface of the outer electrode 2*a* or 2*b* of the detection device 100*b* on the finger 301 is pressed against the surface of the finger 302 in the usage described above with reference to FIG. 11, the other fingers of the same hand as that of the finger 301 do not contact the outer electrode 2*a* or 2*b*. Therefore, a guided signal through the finger 301 and the finger 302 of the opposite hand of the same person is obtained, and a measurement state approximate to the lead I electrocardiogram measurement method is achieved. As a result, a favorable electrocardiogram is obtained.

For example, when the detection device 100*b* is worn on the middle finger of a right hand, the detection device 100*b* is worn such that the insulating part 61 contacts the forefinger of the same right hand and the insulating part 62 contacts the ring finger of the same right hand. Thus, the insulating part 61 or 62 is provided at a part that another finger (forefinger or ring finger) adjacent to the middle finger of the right hand contacts. In other words, the insulating part 61 or 62 is provided at a part where another finger adjacent to a finger wearing the detection device 100*b* contacts the outer electrodes 2*a* and 2*b* on the outer surface.

What is claimed is:

1. A detection device that is wearable on one finger, the detection device comprising:

a first electrode having an inner surface adapted to be in contact with a finger wearing the detection device;

a second electrode provided outside relative to the first electrode when the detection device is worn and electrically insulated from the first electrode;

a light source provided outside relative to the first electrode and inside relative to the second electrode and adapted to irradiate the finger with light;

a light sensor provided outside relative to the first electrode and inside relative to the second electrode and adapted to receive light from the finger;

a control circuit provided outside relative to the first electrode and inside relative to the second electrode and configured to measure biological information based on an output from the light sensor; and an insulating part provided on part of an outer surface of the second electrode, wherein the light source includes at least one of a red light source, an infrared light source, a near-infrared light source, and a green light source, part of the second electrode not covered by the insulating part is exposed and part of the second electrode covered by the insulating part is not exposed, the second electrode is provided all around the first electrode of the detection device that has a ring shape, and the insulating part is provided covering two parts of an outer surface of the second electrode, the two parts being opposed to each other in a radial direction of the detection device.

2. The detection device according to claim 1, wherein the first electrode includes a first opening provided at a position corresponding to the light source, and a second opening provided at a position corresponding to the light sensor, light from the light source is adapted to be irradiated through the first opening to the finger, and the light sensor is adapted to receive light through the second opening from the finger.

3. The detection device according to claim 1, wherein on the outer surface of the second electrode, the insulating part is provided at the two parts which are configured to contact another finger adjacent to the finger.

4. The detection device according to claim 1, wherein on the outer surface of the second electrode, the insulating part is not provided at parts configured to not contact another finger adjacent to the finger.

5. The detection device according to claim 1, wherein the second electrode is provided at a part where another finger adjacent to the finger is configured to not contact, and the second electrode is not provided at a part where another finger adjacent to the finger is configured to contact.

6. The detection device according to claim 1, further comprising:

a storage configured to store a distance between a wearing position of the second electrode and a predetermined position of a living body; and a potential difference measurement circuit configured to measure a potential difference between the first electrode and the second electrode, wherein the control circuit is configured to calculate a pulse wave velocity based on the potential difference measured by the potential difference measurement circuit and the distance stored in the storage.

7. The detection device according to claim 6, wherein the control circuit calculates the pulse wave velocity by dividing the distance stored in the storage by a time that is a difference between:

a time point corresponding to a feature point of an electrocardiogram that is a waveform of the potential difference between the first electrode and the second electrode; and a time point corresponding to a feature point of a pulse wave that is biological information measured based on an output from the light sensor.

8. The detection device according to claim 7, wherein the control circuit is configured to measure the biological information including blood pressure information which is given by a predetermined proportional coefficient times the pulse wave velocity.

9. The detection device according to claim 8, further comprising a communication circuit for transmitting data of the blood pressure information to another device.

10. The detection device according to claim 6, further comprising a communication circuit for transmitting data of the pulse wave velocity to another device.

11. The detection device according to claim 1, further comprising a temperature sensor configured to detect temperature of the first electrode, wherein the control circuit is configured to:

calculate a pulse frequency based on an output waveform from the light sensor, transmit data of the pulse frequency to another device when a difference between a change frequency of the temperature detected by the temperature sensor and a variation value of the pulse frequency is in a predetermined range, and not transmit data of the pulse frequency to the other device when the difference is not in the predetermined range.

12. The detection device according to claim 11, further comprising a heat insulating member provided outside relative to the first electrode and inside relative to the second electrode and having a heat insulating property, wherein the heat insulating member covers the first electrode and the temperature sensor.

13. The detection device according to claim 1, further comprising an acceleration sensor configured to detect acceleration applied to the detection device, wherein the control circuit is configured to:

calculate a pulse frequency based on an output waveform from the light sensor, not transmit data of the pulse frequency to another device when a difference between a frequency of change in the acceleration detected by the acceleration sensor and a variation value of the pulse frequency is in a predetermined range, and transmit data of the pulse frequency to the other device when the difference is not in the predetermined range.

14. The detection device according to claim 1, further comprising:

a battery configured to supply electric power to each component in the detection device; and a coil for charging the battery based on an applied magnetic field, wherein the coil includes a winding wire wound around an outer periphery of the first electrode outside relative to the first electrode and inside relative to the second electrode.

15. The detection device according to claim 14, wherein the coil includes a first coil and a second coil, and the first coil and the second coil are provided on opposite sides in a direction in which the finger is inserted into the detection device, and the first coil and the second coil are coupled in parallel to a battery driver that is disposed between the first coil and the second coil.

* * * * *